United States Patent
Liang et al.

(10) Patent No.: US 11,607,376 B2
(45) Date of Patent: Mar. 21, 2023

(54) OIL-IN-WATER MICROEMULSIONS AND THE PREPARATION THEREOF

(71) Applicant: WACKER CHEMIE AG, Munich (DE)

(72) Inventors: Xinyu Liang, Shanghai (CN); Lin Liu, Shanghai (CN)

(73) Assignee: WACKER CHEMIE AG, Munich (DE)

(*) Notice: Subject to any disclaimer, the term of this patent is extended or adjusted under 35 U.S.C. 154(b) by 215 days.

(21) Appl. No.: 16/617,659

(22) PCT Filed: May 27, 2017

(86) PCT No.: PCT/CN2017/086310
§ 371 (c)(1),
(2) Date: Nov. 27, 2019

(87) PCT Pub. No.: WO2018/218417
PCT Pub. Date: Dec. 6, 2018

(65) Prior Publication Data
US 2020/0179246 A1    Jun. 11, 2020

(51) Int. Cl.
| | | |
|---|---|---|
| *A61Q 5/02* | (2006.01) | |
| *A61K 8/06* | (2006.01) | |
| *A61K 8/86* | (2006.01) | |
| *A61K 8/891* | (2006.01) | |
| *A61K 8/898* | (2006.01) | |
| *A61K 8/92* | (2006.01) | |

(52) U.S. Cl.
CPC ............. *A61K 8/068* (2013.01); *A61K 8/062* (2013.01); *A61K 8/86* (2013.01); *A61K 8/891* (2013.01); *A61K 8/898* (2013.01); *A61K 8/922* (2013.01); *A61K 8/925* (2013.01); *A61Q 5/02* (2013.01); *A61K 2800/262* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 5,244,598 | A | 9/1993 | Merrifield et al. |
| 5,578,298 | A | 11/1996 | Berthiaume et al. |
| 5,683,625 | A | 11/1997 | Berthiaume et al. |
| 6,054,523 | A | 4/2000 | Braun et al. |
| 6,180,117 | B1 | 1/2001 | Berthiaume et al. |
| 6,737,444 | B1 | 5/2004 | Liu |
| 2006/0041026 | A1 | 2/2006 | Mahr et al. |
| 2007/0104674 | A1 | 5/2007 | Gordon et al. |
| 2015/0216790 | A1 | 8/2015 | Feng et al. |
| 2016/0271023 | A1 | 9/2016 | Bekemeier et al. |

FOREIGN PATENT DOCUMENTS

| | | |
|---|---|---|
| CN | 101463134 A | 6/2009 |
| WO | 2016133806 A1 | 8/2016 |

OTHER PUBLICATIONS

"High Refractive Index Amphiphilic Phenyl Silicones for Applications in Personal Care", ip.com Journal, West Henrietta, NY, US, Jul. 11, 2014, XP013163897.

R. A. De Carvalho et al: "Properties of chemically modified gelatin films", Brazilian Journal of Chemical Engineering, vol. 23, No. 1, 2006, pp. 45-53, XP055667505.

*Primary Examiner* — Jyothsna A Venkat
(74) *Attorney, Agent, or Firm* — Brooks Kushman P.C.

(57) ABSTRACT

The invention relates to transparent, stable, film-forming oil-in-water microemulsions, and the use of the microemulsions in leave-on products or wash-off products of hair care application. The microemulsions contain an aminoalkyl-functional organopolysiloxane, a silicone resin, optionally a low viscosity oil, and a surfactant composition, are storage stable, and form coherent crosslinked films upon drying.

11 Claims, 1 Drawing Sheet

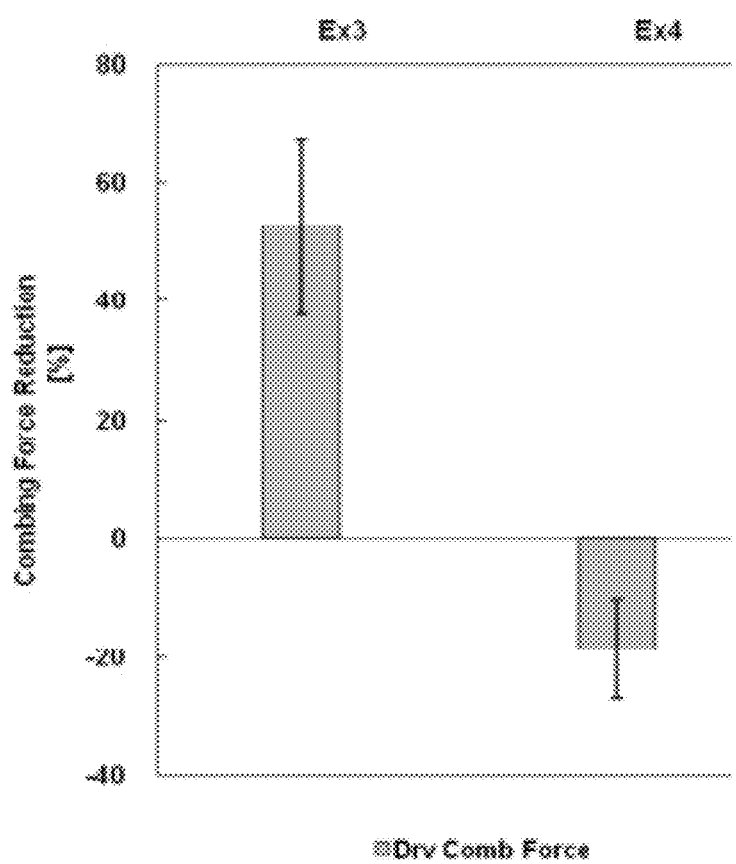

OIL-IN-WATER MICROEMULSIONS AND THE PREPARATION THEREOF

CROSS REFERENCE TO RELATED APPLICATIONS

This application is the U.S. National Phase of PCT Appln. No. PCT/CN2017/086310 filed May 27, 2017, the disclosure of which is incorporated in its entirety by reference herein.

BACKGROUND OF THE INVENTION

1. Field of the Invention

The invention relates to a transparent, stable, film-forming oil-in-water microemulsions and the prepared method thereof.

2. Description of the Related Art

It is known in the art that according to the particle size and appearance, emulsions can be classified into: standard, mini- and micro-emulsions. Standard emulsions have a relatively large particle size (typically greater than 300 nm) and are opaque to the human eye with a milky white appearance. Miniemulsions have a relatively small particle size and is visually observed to have a blue-white to translucent appearance. Microemulsions have a transparent appearance, making it suitable for applications requiring high transparency, and they are the most stable against stratification or sedimentation.

Emulsions of amino-functional silicone fluids and high molecular weight silicones are widely used in hair care compositions. Various types of emulsions have been commercially developed to provide water based products of such amino-functional silicone polymers for use as hair conditioners.

U.S. Pat. No. 5,244,598A discloses a method for preparing amino-functional silicone microemulsions at room temperature by adding water in batches, adding acetic acid to obtain an oil-in-water emulsion with a particle size of about 25 nm, then adding glycerol to adjust the transparency of the emulsion, and finally adding preservatives. However, the state of the final emulsion is not described therein.

U.S. Pat. No. 5,578,298A discloses a process for preparing oil-in-water microemulsions containing high-viscosity (100,000-10,000,000 cs, at 25° C.) amino polysiloxanes. The turbidity of such microemulsions is less than 150. U.S. Pat. No. 5,683,625A discloses a process for preparing oil-in-water microemulsions comprising low amine number (0.01-0.3 meq/g) amino polysiloxanes.

U.S. Pat. No. 6,737,444B1 discloses a method of making an oil-in-water emulsion, wherein an amino-functional silicone fluid and a silicone resin are mixed to form a homogeneous oil phase, to which a surfactant composition is added to obtain a homogeneous mixture, and then water is added to the mixture to cause phase inversion to form an oil-in-water emulsion having a particle size in the range of 100-5,000 nm.

U.S. Pat. No. 6,180,117B1 discloses a process for preparing emulsions of amino-functional silicone fluids and silicone resins, wherein an oil phase containing the silicone resin is mixed with a selected surfactant composition having a specific phase inversion temperature and heated to 70° C., and, while heating, the first portion of the water, acid and the second portion of water are added to obtain an oil-in-water emulsion having a particle size ranging from 5 to 50 nm and a turbidity of less than 150.

SUMMARY OF THE INVENTION

Transparent, stable and film forming O/W microemulsions contain one or more liquid aminoalkyl-containing polyorganosiloxanes A1, one or more silicone resins A2, surfactant composition B and water, wherein,
A1 the polyorganosiloxanes comprise at least 80 mol % of units selected from units of the general formulae Ia, Ib II and III

$$R^1{}_2SiO_{(4-a-b)/2} \quad (Ia),$$

$$R^1{}_a R^2{}_b SiO_{(4-a-b)/2} \quad (Ib),$$

$$R^3{}_3SiO_{(1/2)} \quad (II),$$

$$R^3{}_2 R^4 SiO_{(1/2)} \quad (III),$$

where
a has the value 0 or 1, b has the value 1 or 2, a+b has a value of 2,
$R^1$ represents monovalent hydrocarbyl radicals having 1-40 carbon atoms,
$R^2$ represents
aminoalkyl radicals of the general formula IV

$$-R^5-NR^6R^7 \quad (IV)$$

where
$R^5$ represents divalent hydrocarbyl radicals having 1-40 carbon atoms,
$R^6$ represents monovalent hydrocarbyl radicals having 1-40 carbon atoms, H, hydroxymethyl or alkanoyl radicals, and
$R^7$ represents a radical of the general formula V

$$-(R^8-NR^6)_x R^6 \quad (V)$$

where
x has the value 0 or an integral value from 1 to 40, and
$R^8$ represents a divalent radical of the general formula VI

$$-(CR^9{}_2-)_y \quad (VI)$$

where
y has an integral value from 1 to 6, and $R^9$ represents H or a hydrocarbyl radical having 1-40 carbon atoms,
$R^3$ represents hydrocarbyl radicals having 1-40 carbon atoms and optionally substituted with halogens,
$R^4$ represents —OR or —OH radicals, and
wherein, in the polyorganosiloxanes A1, the average ratio of the sum of units of the general formulae Ia and Ib to the sum of units of the general formulae II and III is in the range from 0.5 to 1000,
wherein II/III≤1, preferably II/III≤0.9,
and the A1 polyorganosiloxanes have an amine number of at least 0.01 meq/g;
one or more silicone resins A2 which each comprise at least 80 mol % of units selected from units of the general formulae VII, VIII, IX and X,

$$R^{10}{}_3SiO_{1/2} \quad (VII),$$

$$R^{10}{}_2SiO_{2/2} \quad (VIII),$$

$$R^{10}SiO_{3/2} \quad (IX)$$

$$SiO_{4/2} \quad (X)$$

wherein

R$^{10}$ represents hydrocarbyl radicals having 1-40 carbon atoms, optionally substituted with halogens, or H, —OR or —OH radicals, at least 20 mol % of the units are selected from units of the general formulae IX and X and at most 10% by weight of the R$^{10}$ radicals are —OR and —OH radicals, based on total weight of A2 the silicone resins.

BRIEF DESCRIPTION OF THE DRAWING

FIG. 1 illustrates a reduction in dry combing force achieved with O/W emulsions of the present invention.

DETAILED DESCRIPTION OF THE PREFERRED EMBODIMENTS

The "film-forming" water-in-oil microemulsion in the invention refers to a microemulsion capable of forming a solid film (with higher crosslinking degree) insoluble in oils after drying, for example by following steps of "Film-forming Experiment" in the present specification.

In microemulsions according to the invention, the turbidity preferably ranges from 0 to 70, preferably from 0 to 50, as measured according to USEPA Method No. 180.1.

The microemulsions, after storage at 48° C. for 30 days, are preferably visually transparent and free off loc, and exhibit no phase separation and no yellowing.

In the microemulsions the average molecular weight Mn of the silicone resins A2 is preferably lower than 5000.

In the microemulsions, the mole ratio of alkoxy and hydroxyl groups in the polyorganosiloxanes A1, to that of the silicone resins A2 is preferably between 0.05-18.4.

In the microemulsions, the surfactant composition B are preferably combinations containing two or more of polyoxyethylene lauryl ether, polyoxyethylene cetyl ether, polyoxyethylene stearyl ether, polyoxyethylene tridecyl ether, $C_{11}$-$C_{15}$ polyoxyethylene alkyl ether and polyoxyethylene oleyl ether.

The microemulsions preferably contain the polyorganosiloxanes A2, silicone resins A2, optional low-viscosity oil A3, and surfactant composition B; wherein surfactant composition B is the composition containing 3 components of polyoxyethylene tridecyl ether, $C_{11}$-$C_{15}$ polyoxyethylene alkyl ether and polyoxyethylene lauryl ether, the calculated average HLB value of surfactant composition B ranging from 12.5 to 13.

The microemulsions preferably contain 10-20 wt % of one or more polyorganosiloxanes A1, 0.4-4 wt % of one or more silicone resins A2, 8-12 wt % of surfactant composition B, and water, based on the total weight of the microemulsions.

In the microemulsions, the optional low-viscosity oil A3 which form homogeneous phase with the polyorganosiloxanes A1 and silicon resins A2, are selected from hydrocarbons, animal or vegetable oils or organopolysiloxane, preferably low molecular weight oligomeric polydialkylsiloxanes or cyclic siloxanes, more preferably oligomeric linear organopolysiloxanes.

The microemulsions can be used in "leave on" products or "wash off" products for hair care application.

The amine number herein refers to the amount of 1N HCl required to neutralize the amino groups in 1 g of amino compounds, measured in meq/g. The average amine number of the polyorganosiloxanes A1 is from 0.001 to 10.0 meq/g, preferably from 0.1 to 5.0 meq/g. The viscosity of the polyorganosiloxanes A1 is between 100-300,000 mPa·s, preferably between 100-10,000 mPa·s as measured according to DIN 53019 at 25° C.

The hydroxyl and alkoxy groups of the polyorganosiloxanes A1 and that of the silicone resin A2 can provide crosslinking. Based on otherwise identical conditions, when II/III≤1, there are more hydroxyl and alkoxy groups in the polyorganosiloxanes A1 than that when II/III>1. More crosslinking can be thus provided, enabling the formation of a film having a higher degree of crosslinking.

The optional low-viscosity oil A3 herein which could form homogeneous phase with the polyorganosiloxanes A1 and the silicone resins A2, has a viscosity of less than 100 mm$^2$/s as measured according to DIN 51562, more preferably less than 10 mm$^2$/s, most preferably less than 5 mm$^2$/s, and may be one of hydrocarbons, animal or vegetable oils or organopolysiloxane. The organopolysiloxane is preferably an oligomeric polydialkylsiloxane or cyclic siloxane, more preferably organopolysiloxane with methyl groups attached to the silicon atoms, yet more preferably a low molecular weight oligomeric polydimethylsiloxane or cyclic polydimethylsiloxane or those with other alkyl, aryl, alkaryl, and aralkyl groups, for example, phenyl groups, benzyl groups, $C_1$-$C_{18}$ alkyl groups, and the like. The greatest preference is given to linear trimethylsilyl terminated polydimethylsiloxanes having on average from 2 to 50 silicon atoms in the organopolysiloxane backbone inclusive of the trimethylsilyl end groups.

Preference is given to volatile organopolysiloxanes having a volatility, measured in accordance with DIN53249, within the following ranges: as the mixture evaporates, weight reduction by 10-80% (preferably 20-70%) after 5 minutes and by 60-99.5% (preferably 70-90%) after 20 minutes, based on the total weight of mixture before evaporating. The volatile organopolysiloxanes can be selected from oligomeric linear organopolysiloxanes with at most about 6 to 10 silicon atoms in the organopolysiloxane backbone or cyclic organopolysiloxanes having from 3 to 6 silicon atoms. The substituents on silicon atoms of oligomeric linear organopolysiloxanes are aryl groups, $C_1$-$C_{18}$ alkyl groups, preferably $C_{1-4}$ alkyl groups, more preferably methyl, or functional groups which do not interfere with the stability of the emulsions or with the ability to use these in cosmetic formulations. The cyclic organopolysiloxanes having from 3 to 6 silicon atoms are selected from hexamethylcyclotrisiloxane, octamethylcyclotetrasiloxane, decamethylcyclopentasiloxane, dodecamethylcyclohexasiloxane, and the like.

The said oil phase herein comprises polyorganosiloxanes A1, silicone resins A2 and optional low-viscosity oil A3, not containing surfactant B, not containing optional glycerol, not containing optional phenoxyethanol.

Calculated amine number of the oil phase=(weight of amino fluid α*amine number of amino fluid α+weight of amino fluid β*amine number of amino fluid β+weight of amino fluid γ*amine number of amino fluid γ+ . . . )/(weight of oil phase).

The surfactant composition B employed in the invention may comprise one or more nonionic surfactants, ionic surfactants, amphoteric surfactants or mixtures thereof, preferably nonionic surfactants.

Typically, non-ionic surfactants should be those containing no silicon atoms. Preferred are alkyl polyether surfactants, preferably alcohol ethoxylates, more preferably fatty alcohol ethoxylates. Fatty alcohol ethoxylates typically contain the characteristic group —(OCH$_2$CH$_2$)$_p$OH, which is attached to an aliphatic hydrocarbon group containing about 8 to 20 carbon atoms, such as lauryl ($C_{12}$), cetyl ($C_{16}$) and stearyl ($C_{18}$). While the value of "p" may range from 1 to about 100, its value is preferably in the range of from about 3 to 20. Preferred nonionic surfactants are combinations of one or more of polyoxyethylene lauryl ether, polyoxyethylene cetyl ether, polyoxyethylene stearyl ether, polyoxyethylene tridecyl ether, $C_{11}$-$C_{15}$ polyoxyethylene alkyl ether and polyoxyethylene oleyl ether. These fatty alcohol ethoxylates are available as commercial products under trade names such as ALFONIC®, BRIJ®, GENAPOL®, NEODOL®, SURFONIC®, TERGITOL®, TRYCOL®, SYMPATENS® and LUTENSOL®.

The calculated average HLB value of the surfactant composition employed in the invention=(HLB value of surfactant 1*weight of surfactant 1+HLB value of surfactant 2*weight of surfactant 2+ . . . )/(weight of surfactant 1+weight of surfactant 2+ . . . ).

In the preparation method herein, the calculated amine number of the oil phase formed with the polyorganosiloxanes A1, silicone resins A2 and optional low-viscosity oil A3, ranges from 0.1 to 5.0 meq/g, and the calculated average HLB value of surfactant composition B ranges from 10 to 15. Preferably, the calculated amine number of the oil phase ranges from 0.2 to 0.6 meq/g, more preferably from 0.23 to 0.29 meq/g, and the calculated average HLB value of surfactant composition B ranges preferably from 12.5 to 13.

The oil in water microemulsions herein may also comprise phenoxyethanol, the amount of which ranges from 0-1 wt %, preferably 0.5-1 wt %, based on the total weight of microemulsions. The phenoxyethanol is antibacterial and adds in decreasing the turbidity of microemulsions.

The microemulsions disclosed in the invention are stable, transparent and can form a highly cross-linked film. The microemulsions can be widely used in personal care or cosmetic products.

A method for preparing transparent oil-in-water microemulsions comprises the steps of:
(1) mixing A1, A2, B and optionally A3, optionally glycerin, and optionally phenoxyethanol to form a mixture of phase (I) by high-speed dispersers or stirrers;
(2) while mixing, adding acid or acid solution to phase (I) to obtain a mixture of phase (II):
(3) while mixing, adding the first portion of water to phase (II); and
(4) while mixing, adding the second portion of water to the mixture from step 3 and obtaining an oil-in-water microemulsion,
(5) adjusting the pH value of the microemulsion to 6.0-6.5 by NaOH solution.

In above method, steps (2) and (3) can be performed simultaneously.

The time interval between steps (1) and (2) or steps (1) and (2, 3) of the preparation method herein is less than 48 hours, preferably less than 24 hours.

In the above-described method, the acid may be a mineral acid or a carboxylic acid, which can protonate the amino group in the polyorganosiloxanes A1. The mineral acid may be selected from hydrochloric, sulfuric, and phosphoric acid, for example. Examples of suitable carboxylic acid are formic acid, acetic acid, propionic, citric acid, phenylacetic acid, benzoic acid, oxalic acid or lactic acid, preferably formic acid or acetic acid.

Unless otherwise specified, all parts and percentages in the examples are based on weight. Information on the components used in the examples is as follows:

Tergitol™ 15S7, alkyl polyether nonionic surfactant, C11-C15 polyoxyethylene alkyl ether (C11-15, EO 7), HLB 12.1, available from Dow Chemical;

Sympatens-AL/090, alkyl polyether nonionic surfactant, polyoxyethylene lauryl ether (C12, EO 9), HLB 13.6, available from KOLB;

Lutensol®TO 12, alkyl polyether nonionic surfactant, polyoxyethylene tridecyl ether (C13, EO 12), HLB 14.5, available from of BASF;

Phenoxyethanol, available from Schulke;

Amino-functional silicone fluid 1, WACKER® FINISH WR1300, aside chain amino-functional silicone fluid containing terminal hydroxyl or methoxy groups, having an amine number of 0.3 meq/g, II/III=0, and a viscosity of 1,000 mPa·s as tested according to DIN 53019, available from Wacker Chemie AG;

Amino-functional silicone fluid 2, a side chain amino-functional silicone fluid, having an amine number of 0.6 meq/g, 64 mol % $SiMe_3$ end groups, 29 mol % $SiMe_2OH$ end groups, 7 mol % $SiMe_2OMe$ end groups, II/III=1.78, and a viscosity of 1,000 mPa·s as tested according to DIN 53019, available from Wacker Chemie AG;

Low-viscosity silicone fluid, BELSIL® DM1 Plus, having a viscosity of 1.1 $mm^2$/s as tested according to DIN 51562, available from Wacker Chemie AG;

MQ silicone resin, WACKER® BELSIL™ 803, Mn=2700 g/mol, wherein the amount of residual alkoxy and hydroxyl is 3.3 wt %, based on the total weight of silicone resin, available from Wacker Chemie AG.

Preparation Method

Examples and Comparative examples are prepared according to Table 1 under room temperature.

A method for preparing transparent oil-in-water microemulsions comprises the steps of:
(1) mixing A1, A2, B and optional A3, optional glycerin, optional phenoxyethanol to form a mixture of phase (I) by high-speed dispersers IKA Ultra-Turrax T25 digital (3000-6000 rpm) or stirrers IKA Eurostar 20 digital (300 rpm);
(2) while mixing, adding acid or acid solution to phase (I) to obtain a mixture of phase (II):
(3) while mixing, adding the first portion of water to phase (II); and
(4) while mixing, adding the second portion of water to the mixture from step 3 and obtaining an oil-in-water microemulsion,
(5) adjusting the pH value of the microemulsion to 6.0-6.5 by NaOH solution.

In above method, steps (2) and (3) can be performed simultaneously.

In Comparative Example 1, a mixture of phase (I) was prepared, which, followed by standing at room temperature for 48 hours, became gelatinous so that the high-speed disperser could not proceed with the next steps.

In Comparative Example 7, a mixture of phase (I) was prepared, which, followed by standing at room temperature for 48 hours and then next steps, became transparent emulsion.

Determination of size distribution D50 by intensity

Referenced Standards: The method complied with standards ISO 13321, ISO 22412 and 21 CFR Part 11

Equipment used Malvern Nano ZS90 (available from Malvern Instruments Ltd.)

Determination method: At 25° C., the samples were placed in the measuring device.

Determination of turbidity NTU

Referenced Standards: US Environmental Protection Agency (USEPA) Method No. 180.1

Equipment used HACH 1900C (available from HACH USA)

Determination method: At 25° C., the samples were placed directly into the measuring tank for readouts on the turbidimeter.

Compositions used in the Examples and comparative examples are listed in Table 1. Test results are listed in Table 2.

TABLE 1

| Components (wt %) | Ex. 1 | Ex. 2 | Ex. 3 | Ex. 4 | Ex. 5 | Ex. 6 | C. Ex. 7 | Ex. 8 | Ex. 9 | C. Ex. 10 | C. Ex. 1 |
|---|---|---|---|---|---|---|---|---|---|---|---|
| Amino-functional silicone fluid 1 | 19.20 | 16.80 | 16.80 | 16.80 | 17.75 | 16.80 | / | 16.80 | 19.0 | | 16.80 |
| Amino-functional silicone fluid 2 | / | / | / | / | / | / | 16.80 | / | / | 19 | / |
| MQ silicone resin | / | 3.20 | / | / | 1.50 | / | / | 3.20 | / | / | / |
| Low-viscosity silicone fluid | / | / | / | / | 0.75 | / | / | / | / | / | / |
| Tergitol™ 15S7 | 6.00 | 6.00 | 6.00 | 6.00 | 6.00 | 6.00 | 6.00 | 6.00 | 6.00 | 6.00 | 6.00 |
| Sympatens-AL/090 | 3.00 | 3.00 | 3.00 | 3.00 | 3.00 | 3.00 | 3.00 | 3.00 | 3.00 | 3.00 | 3.00 |
| Lutensol® TO 12 | 1.00 | 1.00 | 1.00 | 1.00 | 1.00 | 1.00 | 1.00 | 1.00 | 1.00 | 1.00 | 1.00 |
| Phenoxyethanol | 1.00 | 1.00 | 1.00 | 1.00 | 1.00 | 1.00 | 1.00 | 1.00 | 1.00 | 1.00 | 1.00 |
| Glycerol | 2.00 | 2.00 | 2.00 | 2.00 | 2.00 | 2.00 | 2.00 | 2.00 | 2.00 | 2.00 | 2.00 |
| MQ silicone resin | 0.80 | / | 3.20 | 3.20 | / | 3.20 | 3.20 | / | 0.4 | 0.4 | 3.20 |
| Low-viscosity silicone fluid | / | / | / | 1.60 | / | / | / | / | 1.6 | 1.6 | / |
| Aqueous acetic acid solution | 4.58 | 4.58 | 4.58 | 4.58 | 4.58 | 4.58 | 4.58 | 24.58 | 4.58 | 4.58 | / |
| Water (1$^{st}$ portion) | 20.00 | 20.00 | 20.00 | 20.00 | 20.00 | 20.00 | 20.00 | / | 20.00 | 20.00 | / |
| Water (2$^{nd}$ portion) | 42.42 | 42.42 | 42.42 | 40.82 | 42.42 | 42.42 | 42.42 | 42.42 | 41.42 | 41.42 | / |

TABLE 2

| Components (wt %) | Ex. 1 | Ex. 2 | Ex. 3 | Ex. 4 | Ex. 5 | Ex. 6 | C. Ex. 7 | Ex. 8 | Ex. 9 | C. Ex. 10 | C. Ex. 1 |
|---|---|---|---|---|---|---|---|---|---|---|---|
| Appearance | Trans | Trans | Trans | Trans | Trans | Trans | Trans | Trans | Trans | Trans | / |
| Turbidity (NTU) | 24 | 40 | 31 | 49 | 35 | 39 | 37 | 38 | 27 | 22 | / |
| Calculated average HLB value of surfactants | 12.8 | 12.8 | 12.8 | 12.8 | 12.8 | 12.8 | 12.8 | 12.8 | 12.8 | 12.8 | 12.8 |
| Calculated amine number of oil phase (meq/g) | 0.29 | 0.25 | 0.25 | 023 | 0.27 | 0.25 | 0.50 | 0.25 | 0.27 | 0.54 | 025 |

Film-Forming Experiment 5 g of the transparent microemulsion prepared in Example 9 and Comparative Example 10 were respectively spread on a watch glass having a radius of 4 cm, and stored at 25 C until dried. The evaluation of the degree of film formation is shown in Table 3. The sample in Example 9 contains amino-functional silicone fluid 1, II/III=0, and the molar ratio of the hydroxyl and alkoxy groups of A1 the polyorganosiloxanes to those of A2 the silicone resin, calculated according to NMR tests, is 4.6, enabling the formation of a film having a higher degree of crosslinking.

TABLE 3

|  | Example 9 | Comparative Example 10 |
| --- | --- | --- |
| Film formation after drying | The sample formed a uniform solid film No oil stain appeared on the surface of the watch glass in contact with the sample | The sample formed a liquid-solid mixture with flakes Oil stain appeared obviously on the surface of the watch glass in contact with the sample |
| Film crosslinking degree | High | Low |

Combing Force Test

Hair tresses (10 g, 20 cm) were washed with ether and then with 5% ammonium lauryl sulfate solution. The hair tresses were completely wet with water. Afterwards, 0.7 ml of the sample was evenly applied onto each hair tress, which was fully scrubbed for 30 seconds, allowed to stand for 30 seconds before washing with 35° C. warm water, and hung on a hair rack to be dried naturally. At 22° C./60% r.h., the dried hair tresses were placed on the fixture of an Instron 3365 tensile strength tester and subjected to a combing force test. Each tress was measured continuously for at least 11 times, where 5 groups of data were selected and averaged.

As shown in FIG. 1, the dry-combing force was tested with the basic shampoo formulation (without silicone fluid) and the shampoo formulation added with the substances in Example 3 and Example 4 respectively. A graph was drawn using the basic shampoo formulation as the baseline. It was found that the use of the microemulsion sample in Example 4 reduced the combing force by 47% compare to that of Example 3.

Stability Test

After placed in an oven at 48 C for 30 days, the sample was considered to have good thermal stability if it was visually transparent, no yellowing and free of floc.

0.1 g of a 10 wt % aqueous solution of NaOH or 0.1 g of a 2 wt % aqueous solution of NaCl were added to 10 g of the sample, and scores were made according to the results in Table 1:

| Chemical stability rating | 0.1 g of a 10 wt % aqueous solution of NaOH was added to 10 g of the sample | 0.1 g of a 2 wt % aqueous solution of NaCl was added to 10 g of the sample |
| --- | --- | --- |
| 5 | Visually transparent and free of floc | Visually transparent and free of floc |
| 3 | Translucent with a small amount of floc | Translucent with a small amount of floc |
| 1 | Visibly turbid and flocculent | Visibly turbid and flocculent |

The tests above show that the emulsion products prepared in Examples 1-6, 8 and 9 herein had a good thermal stability and a chemical stability scoring 5.

The invention claimed is:

1. A transparent stable, and film forming O/W microemulsion, comprising liquid aminoalkyl-containing polyorganosiloxanes A1, one or more silicone resins A2, surfactant composition B, and water, wherein, the polyorganosiloxanes A1 comprise at least 80 mol % of units of the formulae Ia, Ib, II and III $$R^1{}_a R^2{}_b SiO_{(4-a-b)/2} \tag{Ib}$$

$$R^3{}_3 SiO_{(1/2)} \tag{II}$$

$$R^3{}_2 R^4 SiO_{(1/2)} \tag{III}$$

where a has the value 0 or 1, b has the value 1 or 2, a+b has a value of 2, $R^1$ represents monovalent hydrocarbyl radicals having 1-40 carbon atoms, $R^2$ represents aminoalkyl radicals of the formula IV $$-R^5-NR^6R^7 \tag{IV}$$

where $R^5$ represents divalent hydrocarbyl radicals having 1-40 carbon atoms, $R^6$ represents monovalent hydrocarbyl radicals having 1-40 carbon atoms, H, hydroxymethyl or alkanoyl radicals, and $R^7$ represents a radical of the formula V $$-(R^8-NR^6)_x R^6 \tag{V}$$

where x has the value 0 or an integral value from 1 to 40, and $R^8$ represents a divalent radical of the formula VI $$-(CR^9{}_2-)_y \tag{VI}$$

where y has an integral value from 1 to 6, and $R^9$ represents H or a hydrocarbyl radical having 1-40 carbon atoms, $R^3$ represents hydrocarbyl radicals having 1-40 carbon atoms optionally substituted with halogens, $R^4$ represents —OR —OH radicals, and wherein, in the polyorganosiloxanes A1, the average ratio of the sum of units of the formulae Ia and Ib to the sum of units of the formulae II and III is in the range from 0.5 to 1000, wherein II/III≤1, and the polyorganosiloxanes A1 have an amine number of at least 0.01 meq/g;

one or more silicone resins A2 which each comprise at least 80 mol % of units of the formulae VII, VIII, IX and X, $$R^{10}{}_3 SiO_{1/2} \tag{VII}$$

$$R^{10}{}_2 SiO_{2/2} \tag{VIII}$$

$$R^{10} SiO_{3/2} \tag{IX}$$

$$SiO_{4/2} \tag{X}$$

wherein $R^{10}$ represents hydrocarbyl radicals having 1-40 carbon atoms optionally substituted with halogens, or H, —OR —OH radicals, at least 20 mol % of the units are selected from units of the formulae IX and X and at most 10% by weight of the $R^{10}$ radicals are —OR and —OH radicals, based on total weight of the silicone resins A2.

2. The microemulsion of claim 1, having a turbidity in the range of from 0 to 70, as measured according to USEPA Method No. 180.1.

3. The microemulsion of claim 1, which after storage at 48° C. for 30 days, is visually transparent and free of floc, and exhibits no phase separation, and no yellowing.

4. The microemulsion of claim 1, wherein the average molecular weight Mn of silicone resin A2 is lower than 5000.

5. The microemulsion of claim 1, wherein the mole ratio of alkoxy and hydroxyl groups in polyorganosiloxanes A1 to that of the silicone resin A2 is between 0.05-18.4.

6. The microemulsion of claim 1, wherein the surfactant composition B comprises two or more of polyoxyethylene lauryl ether, polyoxyethylene cetyl ether, polyoxyethylene stearyl ether, polyoxyethylene tridecyl ether, $C_{11}$-$C_{15}$ polyoxyethylene alkyl ether, and polyoxyethylene oleyl ether.

7. The microemulsion of claim 1, comprising at least one polyorganosiloxane A1, at least one silicone resin A2, optionally one or more low viscosity oils A3, and a surfactant composition B; wherein the surfactant composition B is a composition containing polyoxyethylene tridecyl ether, $C_{11}$-$C_{15}$ polyoxyethylene alkyl ether and polyoxyethylene lauryl ether, the calculated average HLB value of surfactant composition B ranging from 12.5 to 13.

8. The microemulsion of claim 7, comprising 10-20 wt % of one or more polyorganosiloxanes A1, 0.4-4 wt % of one or more silicone resins A2, 8-12 wt % surfactant composition B, and water, based on the total weight of the microemulsion.

9. The microemulsion of claim 1, wherein the optional low-viscosity oil A3 forms a homogeneous phase with polyorganosiloxanes A1 and silicon resins A2, and is one or more of hydrocarbons, animal or vegetable oils or organopolysiloxane.

10. The microemulsion of claim 1, wherein the optional low-viscosity oil A3 comprises a volatile linear or cyclic organopolysiloxane.

11. A leave on or wash off product for hair care application, comprising as one component thereof, a microemulsion of claim 1.

* * * * *

UNITED STATES PATENT AND TRADEMARK OFFICE
CERTIFICATE OF CORRECTION

PATENT NO. : 11,607,376 B2
APPLICATION NO. : 16/617659
DATED : March 21, 2023
INVENTOR(S) : Xinyu Stanley Liang et al.

It is certified that error appears in the above-identified patent and that said Letters Patent is hereby corrected as shown below:

In the Claims

Column 10, Lines 10-11, Claim 1:
After "comprise at least 80mol% of units of the formulae Ia, Ib, II and III"
Insert -- $R^1_2SiO_{(4-2)/2}$    (Ia) --

Signed and Sealed this
Twentieth Day of February, 2024

Katherine Kelly Vidal
*Director of the United States Patent and Trademark Office*